US012761864B2

(12) United States Patent
Lee et al.

(10) Patent No.: US 12,761,864 B2
(45) Date of Patent: Oct. 13, 2026

(54) APPARATUS AND METHOD FOR CONTROLLING A VEHICLE

(71) Applicants: HYUNDAI MOTOR COMPANY, Seoul (KR); KIA CORPORATION, Seoul (KR)

(72) Inventors: Dong Hoon Lee, Hwaseong-si (KR); Mun Seung Kang, Suwon-si (KR); Kug Hun Han, Seoul (KR); Yo Han Kim, Ansan-si (KR)

(73) Assignees: HYUNDAI MOTOR COMPANY, Seoul (KR); KIA CORPORATION, Seoul (KR)

( * ) Notice: Subject to any disclaimer, the term of this patent is extended or adjusted under 35 U.S.C. 154(b) by 50 days.

(21) Appl. No.: 18/677,498

(22) Filed: May 29, 2024

(65) Prior Publication Data

US 2025/0117183 A1 Apr. 10, 2025

(30) Foreign Application Priority Data

Oct. 10, 2023 (KR) ........................ 10-2023-0134469

(51) Int. Cl.
*G06F 3/16* (2006.01)
*A61B 5/00* (2006.01)
(Continued)

(52) U.S. Cl.
CPC ............ *G06F 3/165* (2013.01); *A61B 5/4842* (2013.01); *B60W 50/0097* (2013.01); (Continued)

(58) Field of Classification Search
CPC ....... G06F 3/165; G06F 3/013; A61B 5/4842; B60W 50/0097; B60W 50/14;
(Continued)

(56) References Cited

U.S. PATENT DOCUMENTS

2020/0324073 A1* 10/2020 Rajan Kesavelu Shekar .............. G16H 40/63
2022/0017109 A1 1/2022 Hwang
(Continued)

FOREIGN PATENT DOCUMENTS

WO WO-2020012458 A1 * 1/2020 ............. G16H 50/20
WO 2020040317 A1 2/2020

OTHER PUBLICATIONS (WO 2020012458 A1 English/original—same) (Year: 2020).*

*Primary Examiner* — Harry Y Oh
*Assistant Examiner* — Renee LaRose
(74) *Attorney, Agent, or Firm* — Lempia Summerfield Katz LLC

(57) ABSTRACT

An apparatus for controlling a vehicle includes a communication device to receive first driving information of a front vehicle, at least one sensor to obtain second driving information of a host vehicle, and a processor. The processor is configured to generate real behavior information of the host vehicle based on the second driving information, generate predicted behavior information of the host vehicle based on at least one of the first driving information, the second driving information, or any combination thereof, and determine a manner of outputting a sound based on the real behavior information or the predicted behavior information.

18 Claims, 14 Drawing Sheets

(51) Int. Cl.

| | |
|---|---|
| ***B60W 50/00*** | (2006.01) |
| ***B60W 50/14*** | (2020.01) |
| ***B60W 60/00*** | (2020.01) |
| ***G06F 3/01*** | (2006.01) |
| ***G07C 5/08*** | (2006.01) |
| ***H04R 3/04*** | (2006.01) |

(52) U.S. Cl.
CPC ............. *B60W 50/14* (2013.01); *G06F 3/013* (2013.01); *G07C 5/0833* (2013.01); *H04R 3/04* (2013.01); *B60W 60/001* (2020.02); *H04R 2499/13* (2013.01)

(58) Field of Classification Search
CPC ......... B60W 60/001; B60W 2050/143; B60W 50/0098; B60W 40/09; B60W 40/10; B60W 2050/0052; B60W 2420/403; G07C 5/0833; H04R 3/04; H04R 2499/13; H04R 2430/01; H04S 7/30; B60K 35/00; B60K 35/26
See application file for complete search history.

(56) References Cited

U.S. PATENT DOCUMENTS

| | | | | |
|---|---|---|---|---|
| 2022/0135054 | A1* | 5/2022 | Nakamura | A61B 5/1114 701/1 |
| 2024/0256042 | A1* | 8/2024 | Saito | G06F 3/015 |
| 2025/0065902 | A1* | 2/2025 | Giovanardi | B60W 50/0097 |

* cited by examiner

APPARATUS AND METHOD FOR CONTROLLING A VEHICLE

CROSS-REFERENCE TO RELATED APPLICATION

This application claims the benefit of and priority to Korean Patent Application No. 10-2023-0134469, filed in the Korean Intellectual Property Office on Oct. 10, 2023, the entire contents of which are incorporated herein by reference.

TECHNICAL FIELD

The present disclosure relates to an apparatus and a method for controlling a vehicle. More particularly, the present disclosure relates to an apparatus and a method for controlling a vehicle to minimize the motion sickness effects experienced by an occupant.

BACKGROUND

Motion sickness experienced by an occupant inside a moving vehicle may be caused by a difference between the actual behavior of the vehicle and the stimulation and information perceived by the occupant via his or her five senses. In other words, motion sickness may occur by sensory errors or sensory collisions due to mixed signals received by the brain from the body, inner ears, and eyes, without integration of these senses, because an occupant's gaze does not precisely follow turning or movement of the vehicle.

On some occasions, the gaze of the occupant may not follow the turning behavior of the vehicle. In particular, the motion sickness that the occupant experiences may increase when the gaze of the occupant is focused on a fixed object, such as a smartphone, or when moving through wave swaths, vehicle turns, and speed bumps, which are movements in low-frequency bands making it difficult for the brain of the occupant to integrate or ignore senses.

Accordingly, recently, technology for reducing motion sickness of an occupant has been developed in various forms, such as devices including glasses or a panel for reducing motion sickness. However, this technology forces the occupant to wear the devices for reducing motion sickness while the vehicle is being driven, which causes inconvenience to the occupant. In addition, these devices help reducing the effects caused by motion sickness only when the occupant in a stationary state faces a specific object.

SUMMARY

In view of the foregoing, there is a need to develop technology that can minimize motion sickness without wearing equipment that may cause inconvenience to the occupant.

The present disclosure has been made to solve the above-mentioned problems occurring in the prior art while advantages achieved by the prior art are maintained intact.

Aspects of the present disclosure provide an apparatus and a method for controlling a vehicle to enable an occupant to mitigate sensory collisions to reduce motion sickness by outputting a sound based on real behavior information about the vehicle.

Other aspects of the present disclosure provide an apparatus and a method for controlling a vehicle to enable an occupant to correct an error to reduce motion sickness by outputting a sound based on the behavior of the vehicle, this being performed after predicting the behavior of the vehicle in advance.

Other aspects of the present disclosure provide an apparatus and a method for controlling a vehicle, capable of minimizing motion sickness without wearing equipment, which may cause inconvenience to an occupant, or without a sensed stimulation, by providing information about the behavior of the vehicle using a sound range that the occupant is unable to hear using a sound having an inaudible frequency band.

The technical problems to be solved by the present disclosure are not limited to the aforementioned problems. Any other technical problems not mentioned herein should be more clearly understood from the following description by those of ordinary skill in the art to which the present disclosure pertains.

According to an aspect of the present disclosure, an apparatus for controlling a host vehicle may include a communication device to receive first driving information of a front vehicle, at least one sensor to obtain second driving information of a host vehicle, and a processor. The processor is configured to generate real behavior information of the host vehicle based on the second driving information, generate predicted behavior information of the host vehicle based on at least one of the first driving information, the second driving information, or any combinations thereof, and determine a manner of outputting a sound based on the real behavior information or the predicted behavior information.

According to an embodiment, the processor may generate the real behavior information of the host vehicle by filtering only a behavior in a specific frequency band, which is selected from among the second driving information.

According to an embodiment, the processor may output the sound through an output device based on the determined manner of outputting the sound. The processor may output the sound via an output device when the manner of outputting the sound is determined based on the real behavior information of the host vehicle.

According to an embodiment, the processor may determine a behavior of the front vehicle based on at least one of the first driving information, the second driving information, or any combinations thereof. The processor may calculate a time point at which the host vehicle performs the behavior of the front vehicle and generate the predicted behavior information including the time point and the behavior of the front vehicle.

According to an embodiment, the processor may generate autonomous driving information of the host vehicle based on at least one of the first driving information, the second driving information or any combinations thereof, and generate the predicted behavior information of the host vehicle based on the autonomous driving information.

According to an embodiment, the processor may analyze a driving pattern of a driver based on at least one of the first driving information, the second driving information or any combinations thereof. The processor may generate the predicted behavior information of the host vehicle based on the driving pattern of the driver.

According to an embodiment, the processor may output the sound through an output device based on the determined manner of outputting the sound when the manner of outputting the sound is determined based on the predicted behavior information of the host vehicle.

According to an embodiment, the processor may increase an output intensity of the sound and output the sound through an output device based on the determined manner of outputting the sound, when a gaze of an occupant is determined to be directed to the inside of the host vehicle based on information about the occupant obtained from a camera.

According to an embodiment, the determined manner of outputting the sound may include outputting the sound in an inaudible frequency band. The processor may output the sound in the inaudible frequency band through an output device based on the determined manner of outputting the sound.

According to an embodiment, the processor may receive feedback of a motion sickness extent from an occupant through an input device, calculate a score of the motion sickness extent, shift the sound set from an inaudible frequency band to an audible frequency band when the calculated score of the motion sickness extent is determined as exceeding a reference value, increase an output intensity, determine that the manner of outputting the sound includes outputting the sound in an audible frequency band, and output the sound through an output device based on the determined manner of outputting the sound.

According to another aspect of the present disclosure, a method for controlling a vehicle may include receiving first driving information of a front vehicle and obtaining second driving information of a host vehicle. The method may further include generating real behavior information of the host vehicle based on the second driving information and generating predicted behavior information of the host vehicle based on at least one of the first driving information, the second driving information, or any combinations thereof. The method may further include determining a manner of outputting a sound based on the real behavior information or the predicted behavior information.

According to an embodiment, generating the real behavior information of the host vehicle may include generating the real behavior information of the host vehicle, by filtering only a behavior in a specific frequency band, which is selected from among the second driving information.

According to an embodiment, the method may further include outputting the sound through an output device, based on the determined manner of outputting the sound, when the manner of outputting the sound is determined based on the real behavior information of the host vehicle.

According to an embodiment, generating the real behavior information of the host vehicle may include determining a behavior of the front vehicle based on at least one of the first driving information, the second driving information, or any combination thereof, calculating a time point at which the host vehicle performs the behavior of the front vehicle, and generating the predicted behavior information including the time point and the behavior of the front vehicle.

According to an embodiment, generating the real behavior information of the host vehicle may include generating autonomous driving information of the host vehicle based on at least one of the first driving information, the second driving information or any combination thereof, and generating the predicted behavior information of the host vehicle based on the autonomous driving information.

According to an embodiment, generating the real behavior information of the host vehicle may include analyzing a driving pattern of a driver based on at least one of the first driving information, the second driving information or any combination thereof, and generating the predicted behavior information of the host vehicle based on the driving pattern of the driver.

According to an embodiment, the method may further include outputting the sound through an output device, based on the determined manner of outputting the sound, when the manner of outputting the sound is determined based on the predicted behavior information of the host vehicle.

According to an embodiment, the method may further include increasing an output intensity of the sound and outputting the sound through an output device based on the determined manner of outputting the sound, when a gaze of an occupant is determined to be directed to the inside the host vehicle based on information about the occupant obtained from a camera.

According to an embodiment, the determined manner may further include outputting the sound in an inaudible frequency band. The method may further include outputting a sound in the inaudible frequency band through an output device, based on the determined manner of outputting the sound.

According to an embodiment, the method may further include receiving feedback of a motion sickness extent from an occupant through an input device, calculating a score of the motion sickness shifting the sound set to be in an inaudible frequency band to an audible frequency band, when the calculated score of the motion sickness is determined as exceeding a reference value, increasing an output intensity, determining that the manner of outputting the sound includes outputting the sound in an audible frequency band, and outputting the sound through an output device based on the manner of outputting the sound.

BRIEF DESCRIPTION OF THE DRAWINGS

The above and other objects, features, and advantages of the present disclosure should be apparent from the following detailed description taken in conjunction with the accompanying drawings.

DETAILED DESCRIPTION

Figure 1:
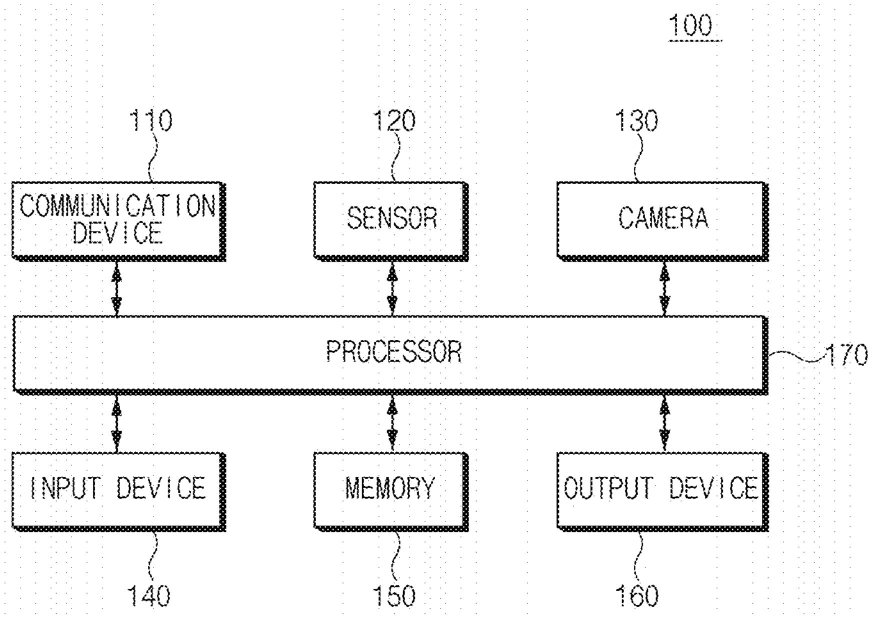
FIG. 1 is a view illustrating the configuration of an apparatus for controlling a vehicle, according to an embodiment of the present disclosure.

Various embodiments of the present disclosure are described in detail below with reference to accompanying drawings. By including the reference numerals to the components of each drawing, it should be noted that the identical or equivalent component is designated by the identical numeral even when they are displayed on other drawings. In addition, in the following description of embodiments of the present disclosure, a detailed description of well-known features or functions is ruled out in order not to unnecessarily obscure the gist of the present disclosure.

In describing the components of the embodiment according to the present disclosure, terms such as first, second, "A", "B", "(a)", "(b)", and the like may be used. These terms are merely intended to distinguish one component from another component. The terms do not limit the nature, sequence, or order of the constituent components. In addition, unless otherwise defined, all terms used herein, including technical or scientific terms, have the same meanings as those generally understood by those of ordinary skill in the art to which the present disclosure pertains. Such terms as those defined in a generally used dictionary are to be interpreted as having meanings equal to the contextual meanings in the relevant field of art and are not to be interpreted as having ideal or excessively formal meanings unless clearly defined as having such in the present application.

Further, when a component, device, element, or the like of the present disclosure is described as having a purpose or performing an operation, function, or the like, the component, device, or element should be considered herein as being "configured to" meet that purpose or perform that operation or function.

FIG. 1 is a view illustrating the configuration of an apparatus for controlling a vehicle, according to an embodiment of the present disclosure.

As illustrated in FIG. 1, an apparatus (vehicle control apparatus) 100 for controlling a vehicle, e.g., a host vehicle, includes a communication device 110, a sensor 120, a camera 130, an input device 140, a memory 150, and an output device 160.

The communication device 110 may include a transceiver to transmit or receive information using an antenna, a communication circuit, or a communication processor. The communication device 110 may communicate with another vehicle (a front vehicle) via vehicle to vehicle (V2V) communication or vehicle to something (V2X) communication.

The sensor 120 may sense various situations for generating behavior information of the vehicle. According to an embodiment, the sensor 120 may obtain driving information including vehicle status information and seat position information. According to an embodiment, the sensor 120 may include a collision sensor, a wheel sensor, a speed sensor, a tilt sensor, a weight sensor, a heading sensor, a yaw rate sensor, a 9-axis acceleration sensor, a gyro sensor, a position module, a vehicle forward/rearward sensor, a tire sensor, a steering sensor, a vehicle internal temperature sensor, an ultrasonic sensor, a radar, a Lidar, an accelerator pedal sensor, a throttle position sensor (TPS), a height sensor, or a seat sensor.

According to an embodiment, the yaw rate sensor, the 9-axis acceleration sensor, and the gyro sensor are provided on the headrest of the seat to be positioned closest to a vestibule organ of the occupant to directly sense the impact of the vehicle behavior on the occupant.

The camera 130 may include an internal camera to obtain an image of the occupant inside a vehicle. The image may be used to obtain information about the direction of the gaze of the occupant. The camera 130 may include an external camera to obtain an external image (e.g., road image) of the vehicle.

The input device 140 may receive an input corresponding to a touch, an operation, or a voice of the occupant. The input device 140 may transmit the input to the processor 170. The processor 170 may control the operation of the vehicle control apparatus based on the input information. According to an embodiment, the input device 140 may include a touch-type input device or a mechanical input device. The input device 140 may be implemented with at least one of a motion sensor or a voice recognizing sensor to sense a motion or a voice of the occupant, or combinations thereof.

The memory 150 may store at least one algorithm to compute or execute various computer-executable instructions for the operation of the vehicle control apparatus according to an embodiment of the present disclosure. According to an embodiment, the memory 150 may store at least one instruction executed by the processor 170. The instruction may allow the vehicle control apparatus to operate according to an embodiment. The memory 150 may include at least one storage medium of at least one a flash memory, a hard disc, a memory card, a Read Only Memory (ROM), a Random Access Memory (RAM), an Electrically Erasable and Programmable ROM (EEPROM), a Programmable ROM (PROM), a magnetic memory, a magnetic disc, or an optical disc.

The output device 160 may output a sound under the control of the processor 170. According to an embodiment, the output device 160 may be implemented with a sound outputting device. According to an embodiment, the output device 160 may include a display device. For example, the output device 160 may include a head up display (HUD) or a cluster. The display device may be implemented with a display that employs a liquid crystal display (LCD) panel, a light emitting diode (LED) panel, an organic light emitting diode (OLED) panel, or a plasma display panel (PDP). The LCD may include a thin film transistor-LCD (TFT-LCD). The display device may be integrally implemented via a touch screen panel (TSP) The details of the output device 160 are be described below with reference to FIGS. 2 to 3.

Figure 2:
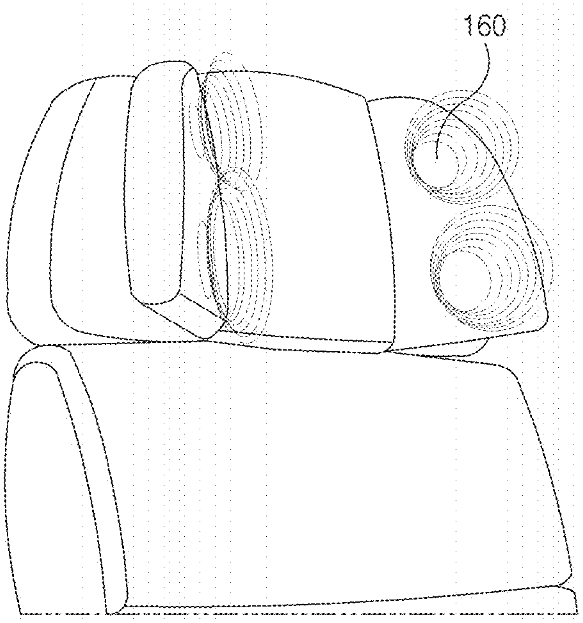
FIGS. 2 and 3 are views illustrating an output device according to an embodiment of the present disclosure.
Figure 3:
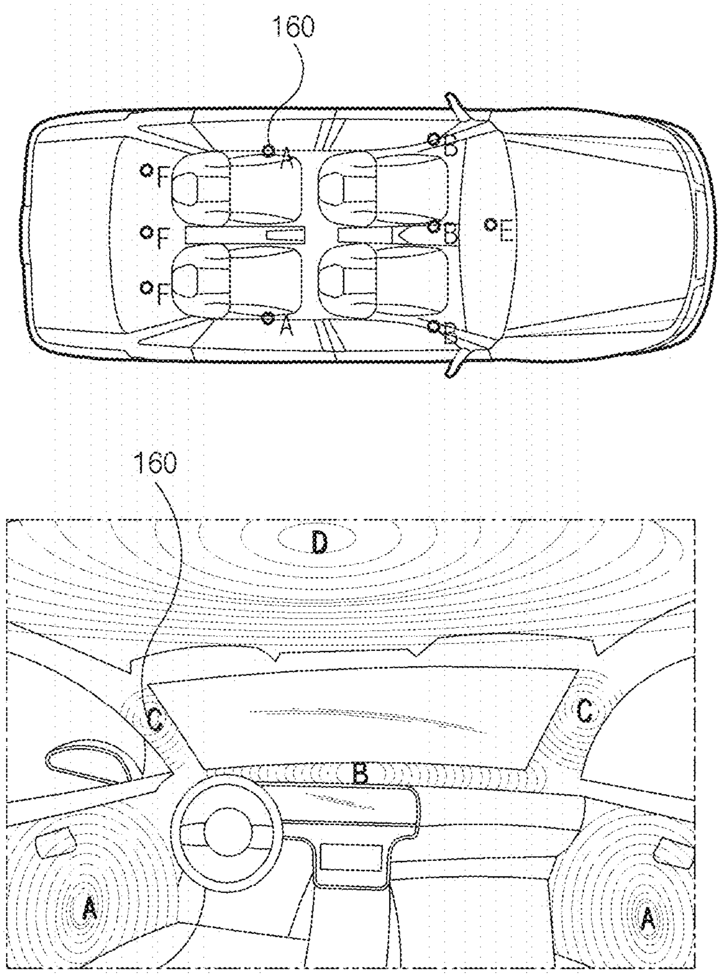

FIGS. 2 and 3 are views illustrating an output device according to an embodiment of the present disclosure.

As illustrated in FIG. 2, the output device 160 may be provided on the headrest of the seat. As illustrated in FIG. 3, the output device 160 may be provided on a vehicle door A, a front speaker B, a vehicle pillar C (e.g., a pillar to connect a body to a roof), a ceiling D, a dashboard E, or a rear shelf F, to generate a stereoscopic sound space and output a high-frequency sound source in an inaudible band. Accordingly, the output device 160 enables the occupant to perceive the behavior of the vehicle without continuously hearing a sound while the vehicle is being driven. According to an embodiment, the output device 160 may output a sound in an audible band that allows the occupant to hear the sound.

The processor 170 may be implemented by various processing devices, such as a microprocessor embedded therein with a semiconductor chip to operate or execute various instructions. The processor 170 may control the vehicle control apparatus according to an embodiment. The processor 170 may be electrically connected to the communication device 110, the sensor 120, the camera 130, the input device 140, the memory 150, and the output device 160 via a wired cable or various types of circuits to transmit an electrical signal including a control command. In addition, the processor 170 may execute an arithmetic operation or data processing related to a control operation and/or communication. The processor 170 may include at least one of a central processing unit, an application processor, a communication processor (CP), or combinations thereof.

The processor 170 may generate real behavior information of a host vehicle, based on driving information obtained by the sensor 120.

According to an embodiment, the processor 170 may generate real behavior information by filtering only a behavior in a specific frequency band, which is selected from among driving information obtained by the sensor 120. The details thereof are described below with reference to FIG. 4.

Figure 4:
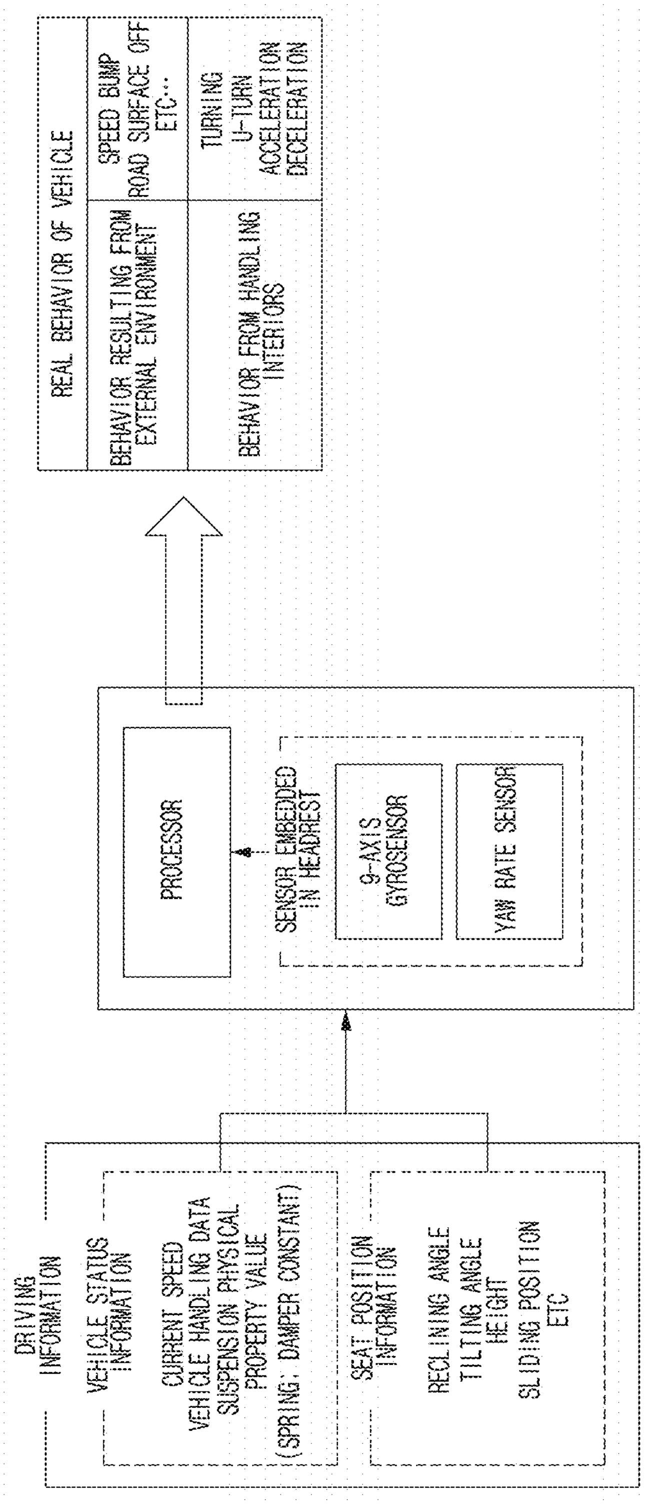
FIG. 4 is a view schematically illustrating a manner for generating real behavior information according to an embodiment of the present disclosure.

FIG. 4 is a view schematically illustrating a manner for generating real behavior information according to an embodiment of the present disclosure.

As illustrated in FIG. 4, the processor 170 may generate real behavior information by filtering only a behavior in a specific frequency band based on information sensed by at least one of the yaw rate sensor, the 9-axis acceleration sensor, the gyro sensor, or combinations thereof, which is selected from the driving information. The driving information may include vehicle status information and seat position information obtained by the sensor 120. In this case, the specific frequency may include a frequency exceeding 0 Hz and equal to or less than 5 Hz. According to an embodiment, the processor 170 may generate the real behavior information about the behavior resulting from an external environment and a behavior, which is handled by the occupant (e.g., a driver), by filtering only the behavior in the specific frequency band. For example, the behavior resulting from the external environment may include the behavior of the vehicle when driving on a road surface, which includes events such as encountering a speed bump and road surface off. The behavior handled by the occupant may include the behavior of the vehicle when turning, performing a U-turn, accelerating, decelerating and the like, which are performed through the operation of a steering wheel, an accelerator pedal, or a brake pedal of the host vehicle by the occupant.

According to an embodiment, the processor 170 may generate predicted behavior information of the host vehicle based on at least one of first driving information of a front vehicle, second driving information of the host vehicle, or combinations thereof. The details thereof are described below with reference to FIG. 5.

Figure 5:
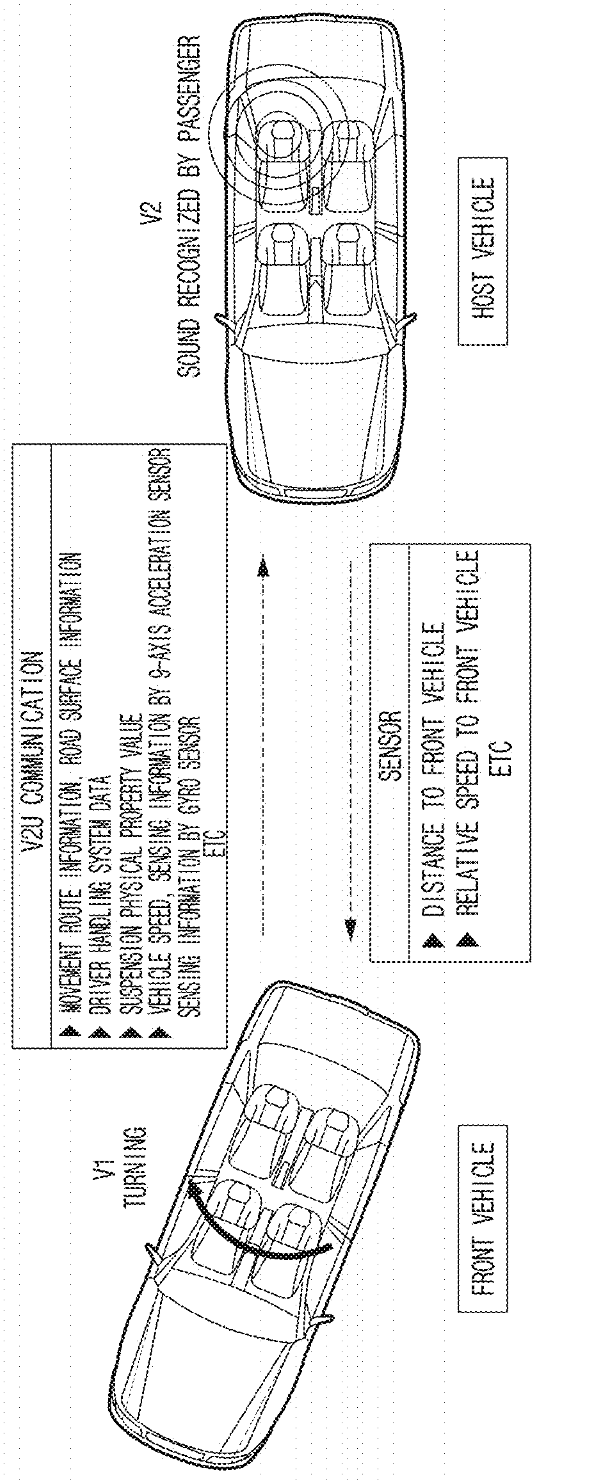
FIG. 5 is a view schematically illustrating a manner for generating predicted behavior information according to an embodiment of the present disclosure.

FIG. 5 is a view schematically illustrating a process for generating predicted behavior information according to an embodiment of the present disclosure.

As illustrated in FIG. 5, the processor 170 may receive first driving information. According to an embodiment, the processor 170 may receive first driving information which includes movement route information, road surface information, driver handling data, a suspension physical property value, a vehicle speed, a 9-axis acceleration sensor detection information (acceleration), or a gyro sensor detection information (angular speed) from the front vehicle V1 through V2V communication. However, the first driving information is not limited thereto. The first driving information may include information obtained by the sensor while the front vehicle is being driven.

The processor 170 may obtain second driving information via the sensor 120. The processor 170 may obtain the second driving information, which includes the distance between the host vehicle V2 and the front vehicle V1 and the relative speed of the front vehicle V1, via the sensor 120. However, the second driving information is not limited thereto, but may include information obtained by the sensor 120 while the host vehicle is being driven. According to an embodiment, the processor 170 may determine the behavior of the front vehicle V1 based on at least one of the first driving information of the front vehicle V1, the second driving information of the host vehicle V2, or combinations thereof. The processor 170 may calculate a time point at which the host vehicle V2 may perform the same behavior as the front vehicle. The processor 170 may generate the calculated time point and predicted behavior information of the host vehicle V2, which may include the previous behavior of the front vehicle V1.

For example, the processor 170 may determine the behavior of the front vehicle V1 as passing through a speed bump and calculate the time point at which the host vehicle V1 passes through the speed bump as 3 seconds after the front vehicle passes through the speed bump. In this case, the processor 170 may generate, as predicted behavior information, an event at which the host vehicle passes through the speed bump at 3 seconds after the front vehicle passes through the speed bump.

According to an embodiment, the processor 170 may generate autonomous driving information of the host vehicle, based on at least one of the first driving information of the front vehicle V1, the second driving information of the host vehicle V2, or combination thereof. The processor 170 may generate the predicted behavior information of the host vehicle V2, based on the dynamics applied to the occupant, based on the position of the occupant based on the autonomous driving information. According to an embodiment, the processor 170 may calculate a static parameter based on at least one of the first driving information of the front vehicle V1, the second driving information of the host vehicle V2, or combinations thereof. The processor 170 may analyze a driving pattern of the driver based on the static parameter and may generate the predicted behavior information of the host vehicle V2, based on the driving pattern of the driver. According to an embodiment, the processor 170 may analyze the driving pattern including intrinsic handling of a driver, an acceleration/deceleration handing pattern, or a brake handling pattern, based on a road state, a traffic situation, or the distance to the front vehicle.

According to an embodiment, the processor 170 may determine the manner or process of outputting the sound through the output device 160 based on the real behavior information or the predicted behavior information of the host vehicle V2. According to an embodiment, the processor 170 may set the sound to a high-frequency sound in an inaudible frequency band.

According to an embodiment, the processor 170 may mitigate the sensory collision by canceling the difference experienced by the occupant by outputting the sound depending on real-time real behavior information, when determining the manner of outputting the sound based on the real behavior information of the host vehicle V2. Accordingly, the motion sickness of the occupant, which may be caused by sensory collision, may be minimized.

According to an embodiment, the processor 170 may enable the occupant to correct the sensory error by outputting a sound through the output device 160 based on the behavior of the front vehicle V1 at a time point, earlier than a time point at which the host vehicle V2 may perform the same previous behavior of the front vehicle V1, by a specific time, such that the occupant predicts the behavior of the host vehicle V2 in advance, when determining the manner of outputting the sound based on the predicted behavior information of the host vehicle V2. For example, when the host vehicle V2 performs the previous behavior of the front vehicle V1 after three seconds have elapsed, the processor 170 may output the sound through the output device 160 depending on the previous behavior of the front vehicle V1 after one second, which is a time point two seconds earlier than three seconds. Accordingly, the processor 170 may enable the occupant to predict the behavior of the host vehicle V2 in advance by outputting the sound through the output device 160 depending on the behavior of the front vehicle V1, at the time point earlier than the time point at which the host vehicle V2 performs the previous behavior of the front vehicle V1, thereby minimizing the motion sickness of the occupant, which results from the sensory error. The more detailed manner for outputting the sound is described below with reference to FIGS. 6 to 8.

Figure 6:
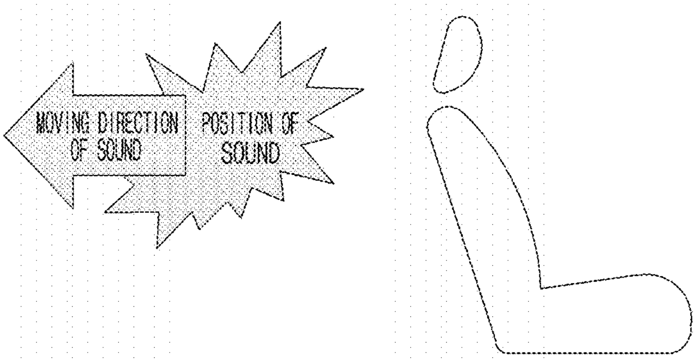
FIGS. 6-8 are views schematically illustrating a manner of outputting a sound determined according to an embodiment of the present disclosure.
Figure 7:
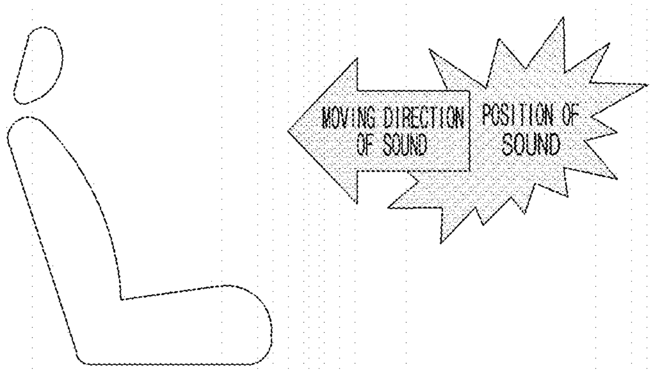
Figure 8:
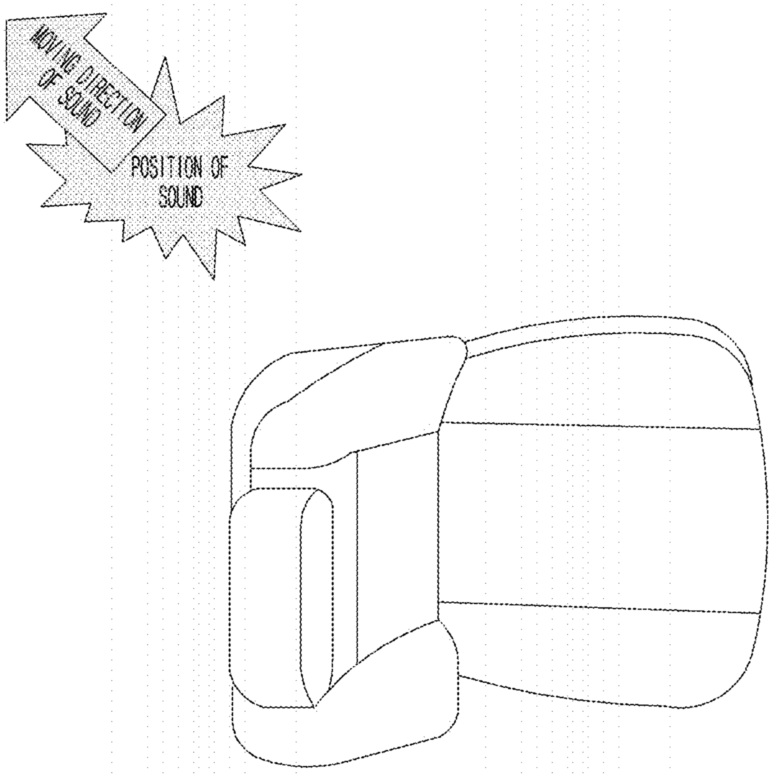

FIGS. 6-8 are views schematically illustrating a manner of outputting a sound determined according to an embodiment of the present disclosure.

As illustrated in FIG. 6, the processor 170 may control a vehicle, e.g., a host vehicle, to calculate a sound output value such that the position of the sound is sensed as being farther away with the acceleration of the vehicle, as the sound is positioned at the rear portion of the occupant. The processor 170 may control the vehicle to output the sound with the calculated sound output value through the output device 160, when the processor 170 determines that the vehicle is being accelerated based on the real behavior information of the vehicle. The front vehicle is determined as being accelerated and the acceleration of the host vehicle is determined as being predicted based on the predicted behavior information of the vehicle. To this end, the processor 170 may calculate the moving direction of the sound, based on the position of the occupant, such that the position of the sound is away from the occupant. The processor 170 may control the vehicle to output the sound through the output device 160 in the calculated moving direction.

As illustrated in FIG. 7, the processor 170 may control the vehicle to calculate a sound output value such that the position of the sound is sensed as being closer with the deceleration of the vehicle, as the sound is positioned in front of the occupant. The processor 170 may control the vehicle to output the sound according to a set calculated sound output value, through the output device 160, when the vehicle is determined as being decelerated based on the real behavior information of the vehicle, and the front vehicle is determined as being decelerated and the deceleration of the host vehicle is determined as being predicted based on the predicted behavior information of the vehicle. To this end, the processor 170 may calculate the moving direction of the sound, based on the position of the occupant, such that the position of the sound is closer to the occupant, and may control to output the sound through the output device 160 in the calculated moving direction.

As illustrated in FIG. 8, the processor 170 may control the vehicle to calculate a sound output value such that the position of the sound is sensed as being farther away with the increase of turning force (the increase of an angular acceleration), as the sound is positioned at the left side of the occupant. The processor 170 may control the vehicle to output the sound through the output device 160, when the vehicle is determined as being turned right based on the real behavior information of the vehicle, and the front vehicle is determined as being turned right and the right turn of the host vehicle is determined as being predicted, based on the predicted behavior information of the vehicle. To this end, the processor 170 may calculate the moving direction of the sound, based on the position of the occupant, such that the position of the sound is away from the occupant. The processor 170 may control the vehicle to output the sound through the output device 160 in the calculated moving direction.

According to an embodiment, the processor 170 may determine whether the gaze of the occupant faces the interior of the vehicle based on the gaze information of the occupant, which is obtained by the camera.

The processor 170 may control the vehicle to output the sound having an increased intensity through the output device 160, when the gaze of the occupant faces the interior of the vehicle. According to an embodiment, the gaze of the driver should face the exterior of the vehicle. Accordingly, on the assumption that the output intensity of a sound is maintained to a first value while outputting the sound, the processor 170 may set the output intensity of the sound to a value exceeding an output intensity (a first value) of the sound output from a driver seat. The processor 170 may control the vehicle to output the sound having the set output intensity through the output device 160. Accordingly, the sensory collision experienced by the occupant may be mitigated when the gaze of the occupant faces the interior of the vehicle.

When the gaze of the occupant does not face the interior of the vehicle (the gaze of the occupant faces the exterior of the vehicle), the processor 170 may control to output the sound having the output intensity maintained to the first value through the output device 160.

According to an embodiment, the processor 170 may output a guide message for requesting feedback of the motion sickness extent through the output device 160. The processor 170 may receive the feedback of the motion sickness extent experienced by the occupant. When the occupant inputs the feedback information through the input device 140, the processor 170 may calculate the score of the motion sickness extent based on the feedback information.

The processor 170 may determine whether the calculated score of the motion sickness extent exceeds a reference value. When the calculated score of the motion sickness is determined as exceeding the reference value, the processor 170 may determine the motion sickness extent of the occupant as being severe and the processor 170 may shift the sound set to be in the inaudible frequency band to the audible frequency band. The processor 170 may output a sound through the output device 160 by increasing the output intensity by a value greater than the first value. Accordingly, the motion sickness experienced by the occupant may be reduced by maximizing the mitigation extent of the sensory collision of the occupant.

When the calculated score of the moving sickness is determined not to exceed the reference value, the processor 170 may determine the motion sickness extent of the occupant as not being severe. The processor 170 may control the vehicle to output the sound having the output intensity maintained to the first value while the sound is maintained in the inaudible frequency band through the output device 160.

FIGS. 9-13 are views illustrating a method for controlling a vehicle, e.g., a host vehicle, according to an embodiment of the present disclosure.

Figure 9:
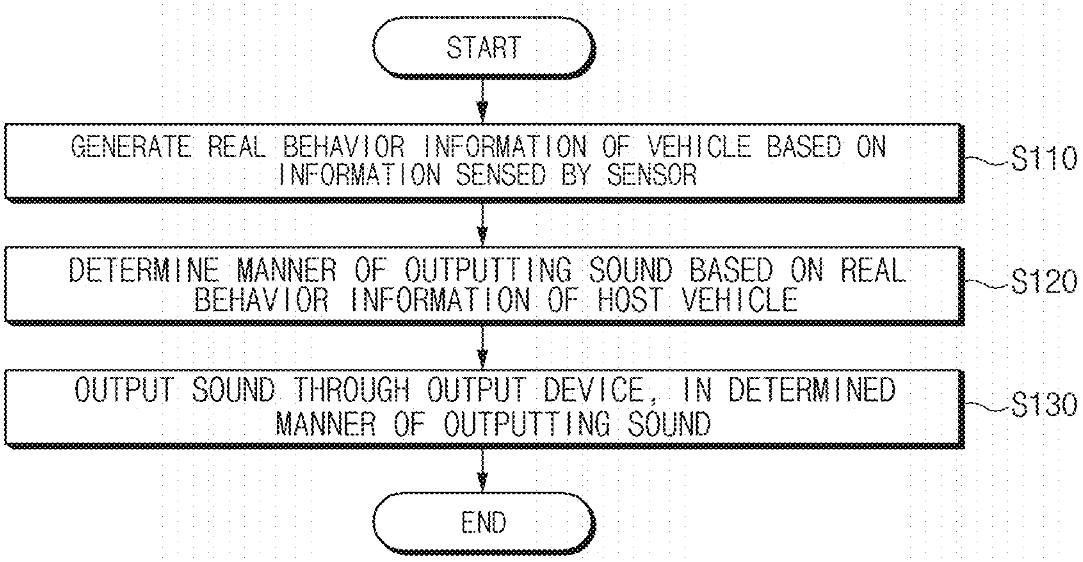
FIGS. 9-13 are views illustrating a method for controlling a vehicle, according to an embodiment of the present disclosure.

As illustrated in FIG. 9, the processor 170 may generate real behavior information of the vehicle by filtering only a behavior in a specific frequency band based on information sensed by at least one of the yaw rate sensor, the 9-axis acceleration sensor, the gyro sensor, or combinations thereof. The real behavior information is determined based on the driving information including vehicle status information and seat position information obtained by the sensor 120 (S110). In this case, the specific frequency may include a frequency exceeding 0 Hz and equal to or less than 5 Hz. According to an embodiment, the processor 170 may generate the real behavior information about the behavior resulting from an external environment and a behavior, which is handled by the occupant (driver), by filtering only the behavior in the specific frequency band For example, the behavior resulting from the external environment may include the behavior of the vehicle in a state of driving on a road surface, which includes events such as a speed bump and road surface off, and the behavior handled by the occupant may include the behavior of the vehicle when turning, performing a U-turn, accelerating, and decelerating, which is performed via the operation of a steering wheel, an accelerator pedal, or a brake pedal by the occupant.

The processor 170 may determine the manner of outputting the sound through the output device 160 based on the real behavior information about the host vehicle (S120). According to an embodiment, the determined manner of outputting the sound may include setting, by the processor 170, the sound to a high-frequency sound in an inaudible frequency band.

The processor 170 may output the sound through the output device 160 in the determined manner of outputting the sound (S130). According to an embodiment, the processor 170 may mitigate the sensory collision by canceling the sensory difference of the occupant by outputting the sound depending on real-time real behavior information, when the manner of outputting the sound is based on the real behavior information of the host vehicle. Accordingly, the motion sickness of the occupant, which may be caused by sensory collision, may be minimized.

Figure 10:
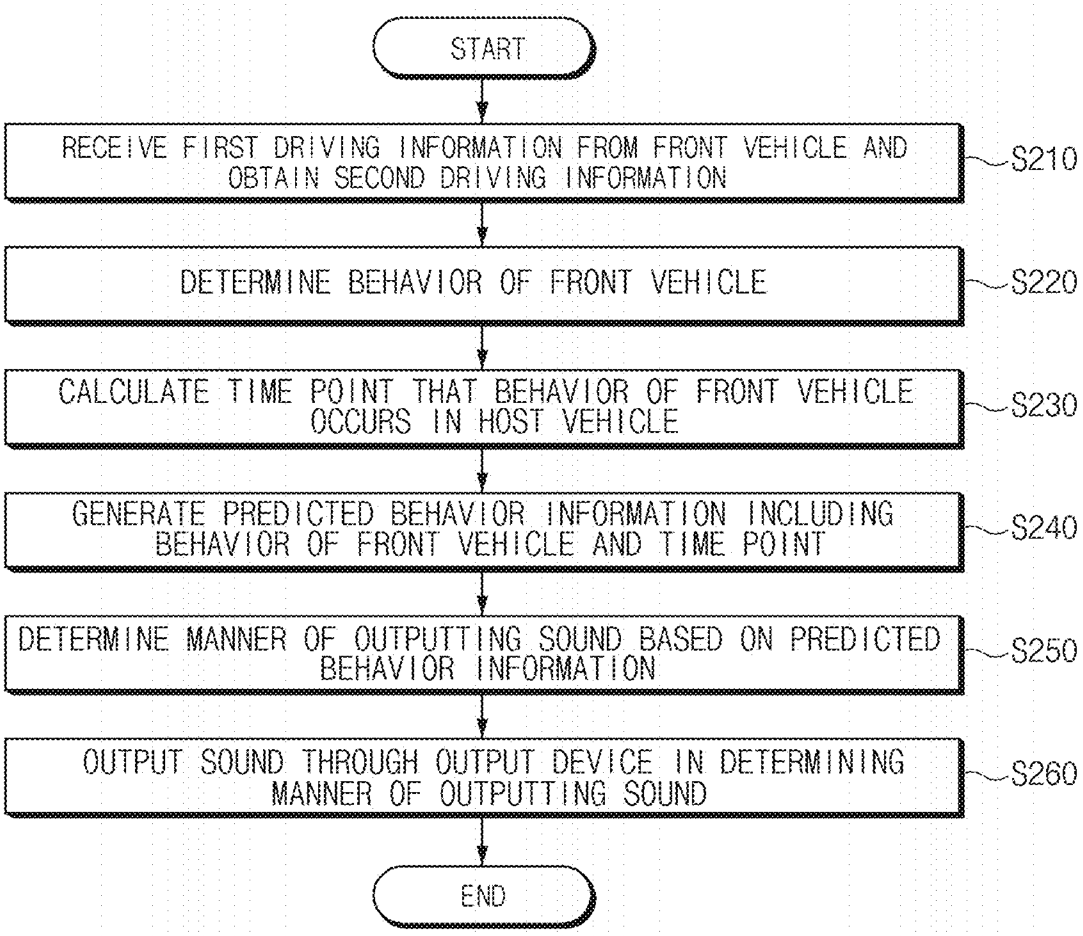

As illustrated in FIG. 10, the processor 170 may receive the first driving information from a front vehicle V1 through the V2V communication (S210). According to an embodiment, the processor 170 may receive first driving information, which includes movement route information, road surface information, driver handling data, a suspension physical property value, a vehicle speed, a 9-axis acceleration sensor detection information (acceleration), or a gyro sensor detection information (angular speed), from the front vehicle V1 through V2V communication. The processor 170 may obtain second driving information through the sensor 120, in S210. The processor 170 may obtain the second driving information, which includes the distance between the host vehicle V2 and the front vehicle V1 and the relative speed of the front vehicle V1, through the sensor 120.

According to an embodiment, the processor 170 may determine the behavior of the front vehicle, based on at least one of first driving information of the front vehicle, second driving information of the host vehicle, or the combination thereof (S220).

The processor 170 may calculate a time point at which the host vehicle V2 performs the previous behavior of the front vehicle (S230).

The processor 170 may generate the calculated time point and predicted behavior information of the host vehicle V2, which includes the previous behavior of the front vehicle (S240).

For example, the processor 170 may determine the previous behavior of the front vehicle V1 as passing through a speed bump. The processor 170 may calculate the time point at which the host vehicle V2 may pass through the speed bump as three seconds elapsed after the front vehicle V1 has passed through the speed bump. In this case, the processor 170 may generate, as predicted behavior information, an event at which the host vehicle V2 passes through the speed bump three seconds after the front vehicle v1 has previously passed through the speed bump.

The processor 170 may determine the manner of outputting the sound through the output device 160 based on the predicted behavior information about the host vehicle (S250). According to an embodiment, the determined manner may include setting, by the processor 170, the sound to a high-frequency sound in an inaudible frequency band.

The processor 170 may output the sound through the output device 160 in the determined manner of outputting the sound (S260).

In S260, the processor 170 may enable the occupant to correct the sensory error by outputting the sound in the determined manner through the output device 160 based on the previous behavior of the front vehicle V1 at a specific time point that is earlier than a time point at which the host vehicle V2 may perform the previous behavior of the front vehicle V1. Thus, the occupant may predict the behavior of the host vehicle V2 in advance, when the manner of outputting the sound is determined based on the predicted behavior information of the host vehicle. For example, when the host vehicle V2 is expected to perform the previous behavior of the front vehicle V1 after three seconds have elapsed from the time in which the front vehicle V1 has passed through the speed bump, the processor 170 may output the sound through the output device 160 depending on the previous behavior of the front vehicle V1 after one second has elapsed. Specifically, one second is a time point two seconds earlier than three seconds, which is the time point at which the host vehicle V2 is expected to pass through the speed bump. Accordingly, the processor 170 may allow the occupant to predict the behavior of the vehicle in advance by outputting the sound through the output device 160 depending on the behavior of the front vehicle V1, at the specific time point earlier than the time point at which the host vehicle V2 is expected to perform the previous behavior of the front vehicle V1. Thereby, the motion sickness experienced by the occupant, which may be caused by sensory error, is minimized.

Figure 11:
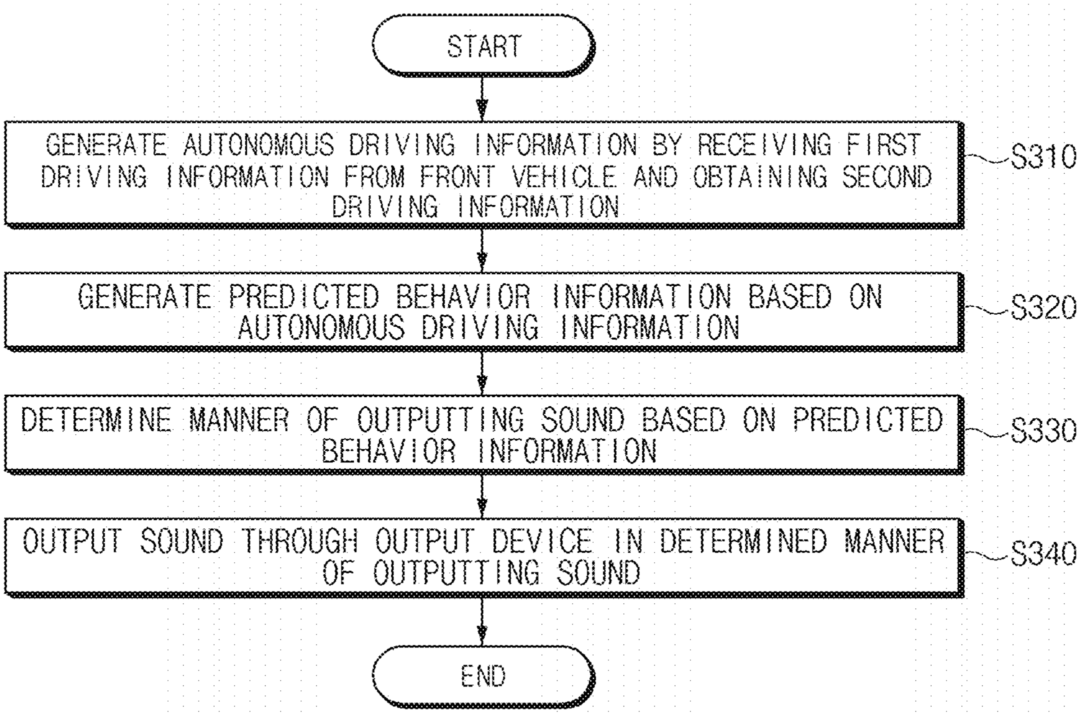

As illustrated in FIG. 11, the processor 170 may obtain the first driving information of the front vehicle and the second driving information of the host vehicle. The processor 170 may generate autonomous driving information of the host vehicle based on at least one of the first driving information of the front vehicle, the second driving information of the host vehicle, or combinations thereof (S310).

The processor 170 may generate the predicted behavior information of the host vehicle based on the autonomous driving information (S320).

The processor 170 may determine a manner of outputting the sound through the output device 160 based on the predicted behavior information about the host vehicle (S330). According to an embodiment, the determined manner may include, setting, by the processor 170, the sound to a high-frequency sound in an inaudible frequency band.

The processor 170 may output the sound through the output device 160 in the determined manner of outputting the sound (S340).

In S340, according to an embodiment, the processor 170 may enable the occupant to correct the sensory error by outputting the sound through the output device 160 based on the behavior of the front vehicle V1 at a time point earlier than a time point at which the host vehicle V2 may perform the previous behavior of the front vehicle V1, by a specific time, such that the occupant predicts the behavior of the host vehicle V1 in advance. For example, prior to when the host vehicle V2 is expected to perform the behavior of the front vehicle V1 after three seconds are elapsed, the processor 170 may output the sound through the output device 160 depending on the behavior of the front vehicle V1 at a specific time of one second after the previous behavior of the host vehicle V1, which is a time point two seconds earlier than three seconds. Accordingly, the processor 170 may allow the occupant to predict the behavior of the vehicle in advance by outputting the sound through the output device 160 depending on the behavior of the front vehicle V1, at the time point earlier than the time point at which the host vehicle performs the behavior of the front vehicle V1. Thereby, the motion sickness experienced by the occupant, which is caused by sensory error, is minimized.

Figure 12:
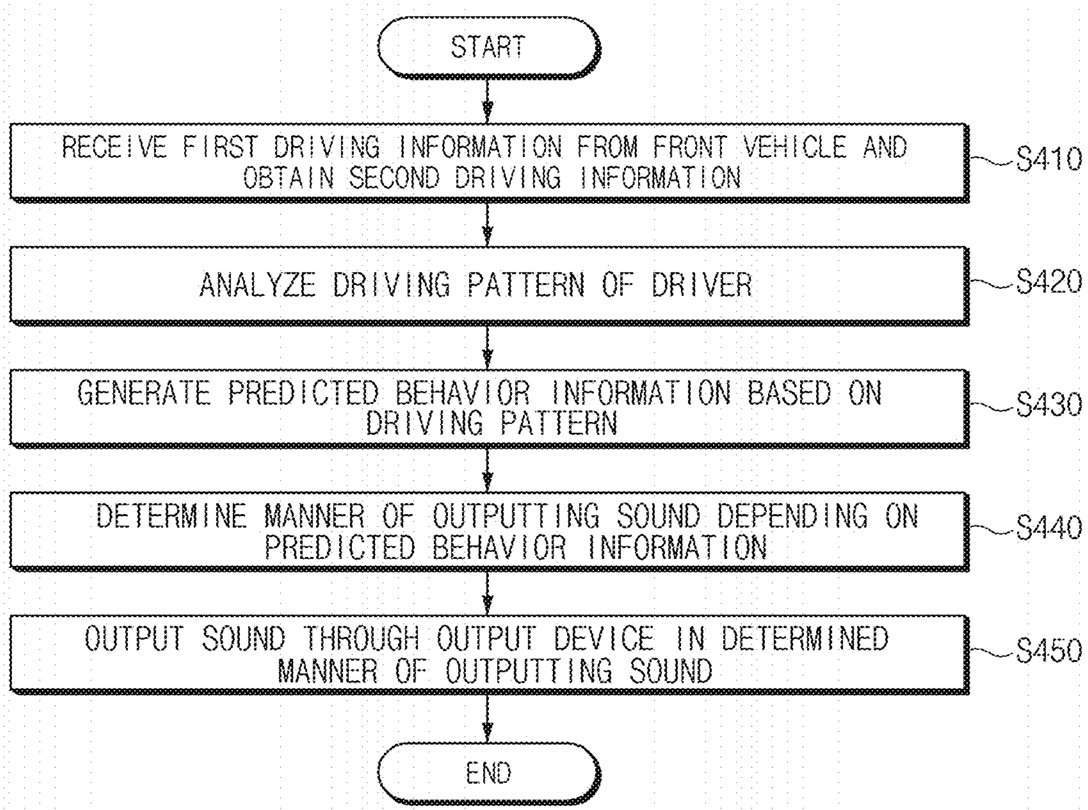

As illustrated in FIG. 12, the processor 170 may obtain the first driving information of the front vehicle V1 and the second driving information of the host vehicle V2 (S410).

The processor 170 may analyze a driving pattern of a driver, based on at least one of the first driving information of the front vehicle, the second driving information of the host vehicle, or combinations thereof (S420). According to an embodiment, the processor 170 may analyze the driving pattern including intrinsic handling of a driver, an acceleration/deceleration handing pattern, or a brake handling pattern, based on a road state, a traffic situation, or the distance to the front vehicle.

The processor 170 may generate the predicted behavior information of the host vehicle based on the driving pattern of the driver (S430).

The processor 170 may determine the manner of outputting the sound through the output device 160 based on the predicted behavior information about the host vehicle V2 (S440). According to an embodiment, the manner of outputting the sound may include, setting, by the processor 170, the sound to a high-frequency sound in an inaudible frequency band.

The processor 170 may output the sound through the output device 160 in the determined manner of outputting the sound (S450).

In S450, according to an embodiment, the processor 170 may enable the occupant to correct the sensory error by outputting the sound through the output device 160 based on the behavior of the front vehicle V1 at a specific time point earlier than a time point at which the host vehicle V2 is expected to perform the previous behavior of the front vehicle V1 such that the occupant predicts the behavior of the host vehicle V2 in advance, when the manner of outputting the sound is determined based on the predicted behavior information of the host vehicle. For example, prior to when the host vehicle V1 is expected to perform the behavior of the front vehicle V1 after three seconds have elapsed, the processor 170 may output the sound through the output device 160 depending on the behavior of the front vehicle V1 at a specific time of one second which is a time point two seconds earlier than three seconds. Accordingly, the processor 170 may allow the occupant to predict the behavior of the host vehicle V2 in advance by outputting the sound through the output device 160 depending on the behavior of the front vehicle V1, at the specific time point earlier than the time point at which the host vehicle is expected to perform the previous behavior of the front vehicle V1. Thereby, the motion sickness experienced by the occupant, which may be caused by the sensory error, is minimized.

Figure 13:
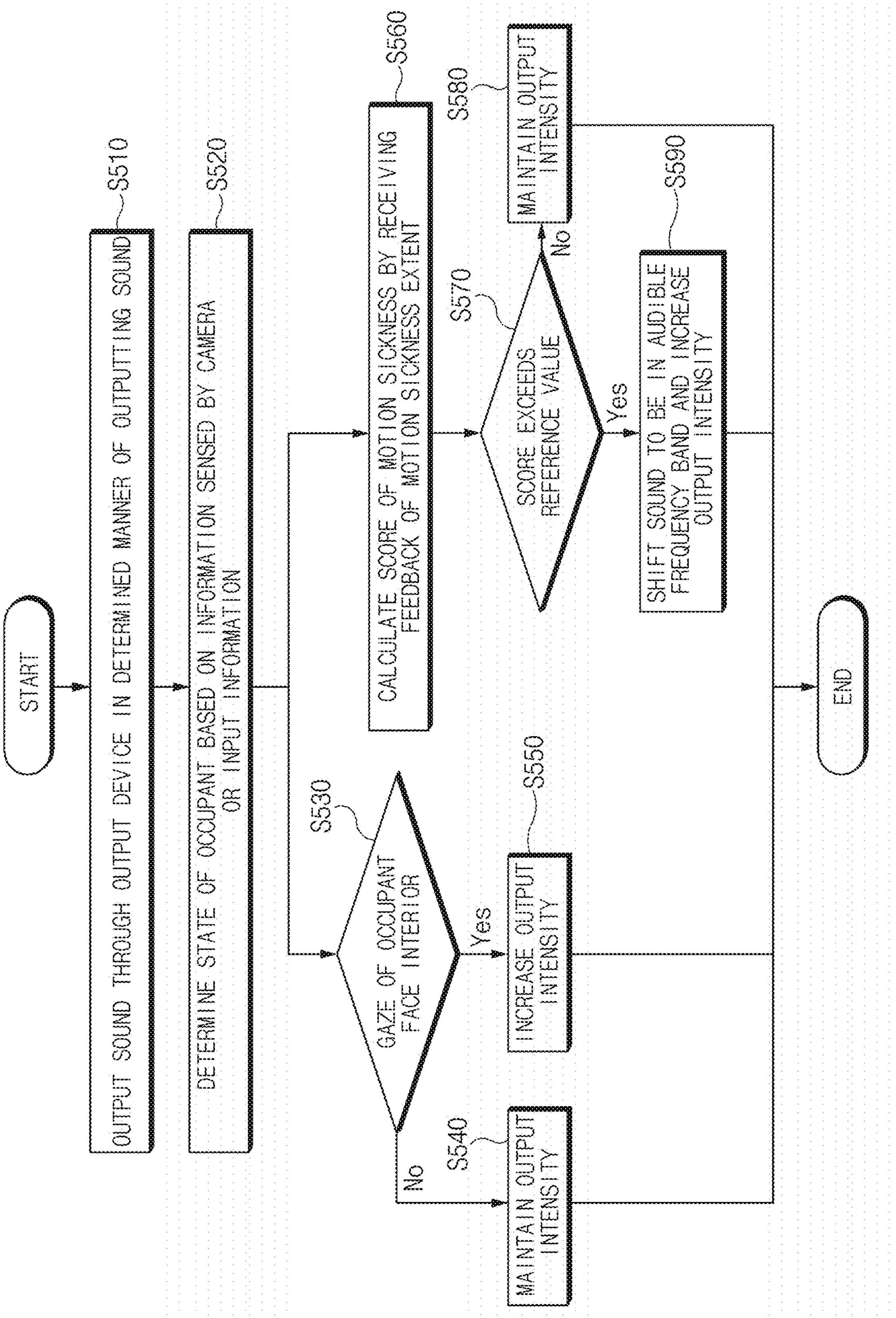

As illustrated in FIG. 13, the processor 170 may output the sound through the output device 160 in the determined manner of outputting the sound (S510).

The processor 170 may determine a state of the occupant based on gaze information of the occupant, which is obtained by the camera 130 or input information, which is input through the input device 140 by the occupant (S520).

The processor 170 may determine whether the gaze of the occupant faces the interior of the vehicle based on the gaze information (S530).

The processor 170 may control the vehicle to output the sound having an increased intensity through the output device 160, when the gaze of the occupant faces the interior of the vehicle (S550).

The processor 170 may control the vehicle to output the sound having the output intensity maintained to the first value through the output device 160, when the gaze of the occupant does not face the interior of the vehicle (the gaze of the occupant faces the exterior of the vehicle) (S540).

The processor 170 may output a guide message for requesting feedback of the motion sickness extent through the output device 160. The processor 170 may receive the feedback of the motion sickness extent experienced by the occupant. When the occupant inputs the feedback information through the input device 140, the processor 170 may calculate the score of the motion sickness extent based on the feedback information (S560).

The processor 170 may determine whether the calculated score of the motion sickness extent exceeds a reference value (S570).

The processor 170 may determine the motion sickness extent of the occupant as being sever and the processor 170 may shift the sound set to be in the inaudible frequency band to the audible frequency band, and output a sound through the output device 160 by increasing the output intensity by a value greater than the first value, when the calculated score of the motion sickness is determined as exceeding the reference value (S590).

The processor 170 may determine the motion sickness extent of the occupant as not being sever, and the processor 170 may control the vehicle to output the sound having the output intensity maintained to the first value while the sound is maintained in the inaudible frequency band through the output device 160, when the calculated score of the moving sickness is determined not to exceed the reference value (S580).

Figure 14:
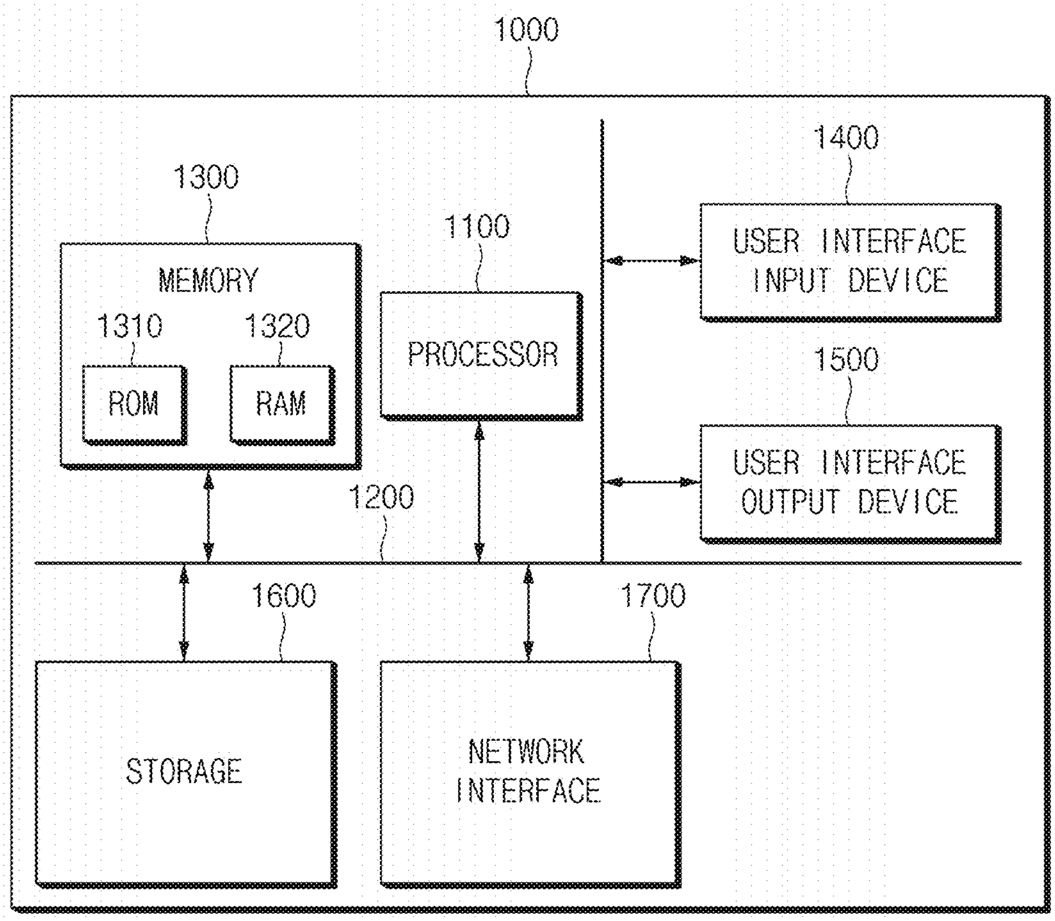
FIG. 14 is a view illustrating the configuration of a computing system to execute a method according to an embodiment of the present disclosure.

FIG. 14 is a view illustrating the configuration of a computing system to execute a method according to an embodiment of the present disclosure.

Referring to FIG. 14, a computing device 1000 may include at least one processor 1100, a memory 1300, a user interface input device 1400, a user interface output device 1500, a storage 1600, and a network interface 1700, which are connected with each other via a system bus 1200.

The processor 1100 may be a central processing unit (CPU) or a semiconductor device for processing instructions stored in the memory 1300 and/or the storage 1600. Each of the memory 1300 and the storage 1600 may include various types of volatile or non-volatile storage media. For example, the memory 1300 may include a read only ROM 1310 and a RAM 1320.

Thus, the operations of the methods or algorithms described in connection with the embodiments disclosed in the present disclosure may be directly implemented with a hardware module, a software module, or the combinations thereof, executed by the processor 1100. The software module may reside on a storage medium (i.e., the memory 1300 and/or the storage 1600), such as a RAM, a flash memory, a ROM, an erasable and programmable ROM (EPROM), an electrically EPROM (EEPROM), a register, a hard disc, a removable disc, or a compact disc-ROM (CD-ROM). The storage medium may be coupled to the processor 1100. The processor 1100 may read out information from the storage medium and may write information in the storage medium. Alternatively, the storage medium may be integrated with the processor 1100. The processor and storage medium may reside in an application specific integrated circuit (ASIC). The ASIC may reside in a user terminal. Alternatively, the processor and storage medium may reside as separate components of the user terminal.

According to an embodiment of the present disclosure, the apparatus and the method for controlling the vehicle enables the occupant to mitigate sensory collision to reduce motion sickness by outputting a sound based on real behavior information about a vehicle.

According to an embodiment of the present disclosure, the apparatus and the method for controlling the vehicle enables the occupant to correct an error to reduce motion sickness by outputting a sound, based on the behavior of the vehicle, which is to be performed after predicting the behavior of the vehicle in advance.

According to an embodiment of the present disclosure, the apparatus and the method for controlling the vehicle enables the motion sickness to be minimized without wearing equipment causing the inconvenience of an occupant or without a stimulation sensed, by providing information about the behavior of the vehicle and by using a sound range that the occupant is unable to hear using a sound having an inaudible frequency band.

The above description is merely an example of the technical idea of the present disclosure, and various modifications and modifications may be made by one of ordinary skill in the art without departing from the essential characteristics of the disclosure.

Therefore, the various embodiments of the present disclosure are provided to explain the spirit and scope of the present disclosure, but not to limit them, so that the spirit and scope of the present disclosure is not limited by the embodiments. The scope of the present disclosure should be construed on the basis of the accompanying claims. All the technical ideas within the scope equivalent to the claims should be included in the scope of the present disclosure.

Hereinabove, although the present disclosure has been described with reference to various embodiments and the accompanying drawings, the present disclosure is not limited thereto, but may be variously modified and altered by those of ordinary skill in the art to which the present disclosure pertains without departing from the spirit and scope of the present disclosure claimed in the following claims.

What is claimed is:

1. An apparatus for controlling a host vehicle, the apparatus comprising:
- a communication device configured to receive first driving information of a front vehicle;
- at least one sensor configured to obtain second driving information of the host vehicle; and
- a processor configured to:
  - generate real behavior information of the host vehicle based on the second driving information;
  - determine a behavior of the front vehicle based on at least one of the first driving information, the second driving information, or any combination thereof;
  - calculate a time point at which the host vehicle performs the behavior of the front vehicle;
  - generate predicted behavior information of the host vehicle including the time point and the behavior of the front vehicle based on at least one of the first driving information, the second driving information, or any combination of the first driving information and the second driving information;
  - determine a manner of outputting a sound based on the real behavior information or the predicted behavior information;
  - output the sound through an output device based on the determined manner of outputting the sound; and
  - determine a state of an occupant based on input information, wherein the input information is input through an input device by the occupant and includes feedback of a motion sickness extent experienced by the occupant.

2. The apparatus of claim 1, wherein the processor is configured to generate the real behavior information of the host vehicle by filtering only a behavior in a specific frequency band, which is selected from among the second driving information.

3. The apparatus of claim 1, wherein the processor is configured to output the sound through the output device, based on the determined manner of outputting the sound, when the manner of outputting the sound is determined based on the real behavior information of the host vehicle.

4. The apparatus of claim 1, wherein the processor is configured to:
- generate autonomous driving information of the host vehicle based on at least one of the first driving information, the second driving information or any combination thereof; and
- generate the predicted behavior information of the host vehicle based on the autonomous driving information.

5. The apparatus of claim 1, wherein the processor is configured to:
- analyze a driving pattern of a driver, based on at least one of the first driving information, the second driving information or any combination thereof; and
- generate the predicted behavior information of the host vehicle based on the driving pattern of the driver.

6. The apparatus of claim 1, wherein the processor is configured to output the sound through the output device based on the determined manner of outputting the sound when the manner of outputting the sound is determined based on the predicted behavior information of the host vehicle.

7. The apparatus of claim 1, wherein the processor is configured to increase an output intensity of the sound and output the sound through the output device based on the determined manner of outputting the sound, when a gaze of the occupant is determined to be directed to inside of the host vehicle based on information about the occupant obtained from a camera.

8. The apparatus of claim 1, wherein the processor is configured to:
- determine that the manner of outputting the sound includes outputting the sound in an inaudible frequency band; and
- output the sound in the inaudible frequency band through the output device based on the determined manner of outputting the sound.

9. The apparatus of claim 1, wherein the processor is configured to:
- receive feedback of the motion sickness extent from the occupant through the input device;
- calculate a score of the motion sickness extent;
- shift the sound previously set to be in an inaudible frequency band to an audible frequency band when the calculated score of the motion sickness extent is determined as exceeding a reference value;
- increase an output intensity;
- determine that the manner of outputting the sound includes outputting the sound in the audible frequency band; and output the sound through the output device based on the determined manner of outputting the sound.

10. A method for controlling a host vehicle, the method comprising:

receiving first driving information of a front vehicle;

obtaining second driving information of the host vehicle;

generating real behavior information of the host vehicle based on the second driving information;

generating predicted behavior information of the host vehicle based on at least one of the first driving information, the second driving information, or any combination thereof;

determining a manner of outputting a sound based on the real behavior information or the predicted behavior information;

outputting the sound through an output device based on the determined manner of outputting the sound; and determining a state of an occupant based on input information, wherein the input information is input through an input device by the occupant and includes feedback of a motion sickness extent experienced by the occupant, wherein generating the real behavior information of the host vehicle includes:

determining a behavior of the front vehicle based on at least one of the first driving information, the second driving information, or any combination thereof;

calculating a time point at which the host vehicle performs the behavior of the front vehicle; and generating the predicted behavior information including the time point and the behavior of the front vehicle.

11. The method of claim 10, wherein generating the real behavior information of the host vehicle includes generating the real behavior information of the host vehicle by filtering only a behavior in a specific frequency band, which is selected from among the second driving information.

12. The method of claim 10, further comprising:

outputting the sound through the output device, based on the determined manner of outputting the sound, when the manner of outputting the sound is determined based on the real behavior information of the host vehicle.

13. The method of claim 10, wherein generating the real behavior information of the host vehicle includes:

generating autonomous driving information of the host vehicle based on at least one of the first driving information, the second driving information, or any combination thereof; and generating the predicted behavior information of the host vehicle based on the autonomous driving information.

14. The method of claim 10, wherein generating the real behavior information of the host vehicle includes:

analyzing a driving pattern of a driver based on at least one of the first driving information, the second driving information, or any combination thereof; and generating the predicted behavior information of the host vehicle based on the driving pattern of the driver.

15. The method of claim 10, further comprising:

outputting the sound through the output device based on the determined manner of outputting the sound, when the manner of outputting the sound is determined based on the predicted behavior information of the host vehicle.

16. The method of claim 10, further comprising:

increasing an output intensity of the sound; and outputting the sound through the output device in the determined manner of outputting the sound, when a gaze of the occupant is determined to be directed to inside the host vehicle based on information about the occupant obtained from a camera.

17. The method of claim 10, wherein:

the determined manner includes outputting the sound in an inaudible frequency band; and the method further comprises outputting the sound in the inaudible frequency band through the output device based on the determined manner of outputting the sound.

18. The method of claim 10, further comprising:

receiving feedback of the motion sickness extent from the occupant through the input device;

calculating a score of the motion sickness extent;

shifting the sound previously set to be in an inaudible frequency band to an audible frequency band when the calculated score of the motion sickness extent is determined as exceeding a reference value;

increasing an output intensity;

determining that the manner of outputting the sound includes outputting the sound in the audible frequency band; and outputting the sound through the output device based on the determined manner of outputting the sound.

* * * * *